US011039750B2

(12) United States Patent
Hendriks et al.

(10) Patent No.: US 11,039,750 B2
(45) Date of Patent: Jun. 22, 2021

(54) NEEDLE WITH OPTICAL FIBERS

(71) Applicant: KONINKLIJKE PHILIPS N.V., Eindhoven (NL)

(72) Inventors: Bernardus Hendrikus Wilhelmus Hendriks, Eindhoven (NL); Augustinus Laurentius Braun, Heeze (NL); Rik Harbers, Zurich (CH); Marjolein Van Der Voort, Valkenswaard (NL); Adrien Desjardins, Eindhoven (NL); Rami Nachabe, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1234 days.

(21) Appl. No.: 15/262,601

(22) Filed: Sep. 12, 2016

(65) Prior Publication Data
US 2016/0374563 A1  Dec. 29, 2016

Related U.S. Application Data

(63) Continuation of application No. 13/129,171, filed as application No. PCT/IB2009/055128 on Nov. 18, 2009, now abandoned.

(30) Foreign Application Priority Data

Nov. 19, 2008  (EP) .................................. 08169409

(51) Int. Cl.
*A61B 17/34*  (2006.01)
*A61B 5/00*  (2006.01)
(Continued)

(52) U.S. Cl.
CPC .......... *A61B 5/0084* (2013.01); *A61B 5/0075* (2013.01); *A61B 5/6848* (2013.01);
(Continued)

(58) Field of Classification Search
None
See application file for complete search history.

(56) References Cited

U.S. PATENT DOCUMENTS 4,566,438 A  1/1986 Liese et al.
5,460,182 A * 10/1995 Goodman ............ A61B 5/0084
600/342
(Continued)

FOREIGN PATENT DOCUMENTS

CN  1784173 A  6/2006
EP  1884211 A2  2/2008
(Continued)

OTHER PUBLICATIONS

Pfefer, T.J. et al., "Computational Analysis of Beveled-Tip Fiber Probes for Selective Detection of Subsurface Fluorophores in Turbid Media", Optical Fibers and Sensors for Medical Applications IV, Proc. of SPIE, vol. 5317, 2004, pp. 206-213.

*Primary Examiner* — Patricia J Park

(57) ABSTRACT

Needle interventions are widely used in the field of oncology for taking biopsies of tissue in order to inspect whether tissue is cancerous or not. To make these interventions more reliable feedback of what kind of tissue is in front of the needle is required. A way to achieve this is by making use of optical spectroscopy. This requires integration of fibers into the needle. These fibers are used to deliver light to illuminate the tissue in front of the needle and to collect back the reflected light from the tissue. The present invention proposes to integrate the fiber distal ends in the slanted bevel of the needle in such a way that at least one source-detector fiber pair has a distance that is larger than the outer diameter of the needle.

16 Claims, 4 Drawing Sheets

(51) Int. Cl.
*A61B 10/02* (2006.01)
*A61B 18/14* (2006.01)
*A61B 17/00* (2006.01)
*A61B 5/1459* (2006.01)

(52) U.S. Cl.
CPC ...... *A61B 10/0233* (2013.01); *A61B 10/0283* (2013.01); *A61B 17/3401* (2013.01); *A61B 18/1477* (2013.01); *A61B 5/1459* (2013.01); *A61B 2017/00057* (2013.01); *A61B 2018/1425* (2013.01)

(56) References Cited

U.S. PATENT DOCUMENTS

| | | | |
|---|---|---|---|
| 7,025,765 | B2 | 4/2006 | Balbierz et al. |
| 7,662,108 | B2 | 2/2010 | Dunker et al. |
| 7,945,312 | B2 | 5/2011 | Hular et al. |
| 2004/0138528 | A1 | 7/2004 | Richter et al. |
| 2005/0261568 | A1* | 11/2005 | Hular ............... A61B 5/0066 600/407 |
| 2008/0009751 | A1* | 1/2008 | Berndt ............... A61B 5/0075 600/478 |
| 2008/0039894 | A1 | 2/2008 | Catanese et al. |

FOREIGN PATENT DOCUMENTS

| | | |
|---|---|---|
| JP | 2006006919 A | 1/2006 |
| WO | 2004082468 A2 | 9/2004 |
| WO | 2005087092 A1 | 9/2005 |

\* cited by examiner

NEEDLE WITH OPTICAL FIBERS

CROSS REFERENCE TO RELATED APPLICATION

This is a continuation of prior application Ser. No. 13/129,171 filed May 13, 2011.

FIELD OF THE INVENTION

The invention generally relates to a needle with optical fibers. Particularly, the invention relates to a small diameter needle for tissue inspection based on optical spectroscopy to diagnose whether tissue is cancerous or not.

TECHNOLOGICAL BACKGROUND

Needle interventions are widely used in the field of oncology for taking biopsies of tissue in order to inspect whether tissue is cancerous or not. To make these interventions more reliable feedback of what kind of tissue is in front of the needle is required. A way to achieve this is by making use of optical spectroscopy. This requires integration of fibers into the needle. These fibers are used to deliver light to illuminate the tissue in front of the needle and to collect back the reflected light from the tissue.

An important feature that can be used in discriminating tissue is the absorption peaks present in the reflectance spectra. In general the absorption of tissue in the visible range is rather low (typically the absorption coefficient $\mu_a=0.1$ cm$^{-1}$). This means that when the source-detector fiber ends are close to each other, the effect of the absorption becomes rather small on the spectra and as a result difficult to detect.

Various needle interventions such as taking biopsies could benefit from this kind of tissue characterization in front of the needle. However, these needle interventions have a strong drive to have needles with an as small as possible outer diameter in order to reduce the trauma of the patient as much as possible. As a result, this drive towards small outer diameter needles is in conflict with the requirement that the fibers should be as far as possible apart in order to have detectable absorption features in the measured reflectance spectra.

Various fiber optic probes are described in literature such as in "Fiber optic probes for biomedical optical spectroscopy" by U. Utzinger and R. R. Richards-Kortum in Journal of Biomedical Optics volume 8 (2003) p 121-147. These probes have in general blunt probe ends resulting in fiber end distances that are smaller than the diameter of the probe.

SUMMARY OF THE INVENTION

It might be an object of the invention to integrate the source-detector fibers into the needle tip such that the outer diameter of the needle is small while still having a detectable absorption feature in the measured reflectance spectra.

These might be achieved by the subject matter according to each of the independent claims. Further embodiments of the present invention are described in the respective dependent claims.

Generally, a needle according to the invention comprises a shaft, a tip at a distal end of the shaft, wherein the tip of the needle is formed by a bevel, a first fiber, the first fiber being capable of transmitting light, wherein an end surface of the first fiber is located at a top of the bevel, and a second fiber, the second fiber being capable of transmitting light, wherein end surface of the second fiber is located at a bottom of the bevel.

The bevel of the needle is in general slanted in order to allow easy entry into the tissue. Therefore, with 'bevel' is meant a geometrical structure allowing for introducing the needle into tissue. Usually, a shaft of a needle includes a circular cross section. The distal end of a needle shaft, in particular of a shaft of a hollow needle, is cut such that an oval surface is formed, which is inclined relative to the longitudinal axis of the shaft. Further, there is defined an angle between the longitudinal axis of the shaft and the inclined surface, i.e. the bevel. The bevel forms a pointed tip at the most distal end of the needle. Furthermore, the edge between the outer surface of the shaft and the inclined surface of the bevel might be sharpened.

The wording 'top of the bevel' should indicate an area being part of the surface of the bevel, which area is located adjacent to the distal edge between the bevel and the shaft. That is, a fiber which is located at the top of the bevel might be located at the long axis of the oval surface of the bevel, near the distal edge, i.e. the pointed tip.

On the other hand, 'bottom of the bevel' means the area being part of the surface of the bevel, which area is located diametric to the top of the bevel. That is, the fiber which is located at the bottom of the bevel might be on or near or adjacent beside the long axis of the oval surface of the bevel near the proximal edge between bevel and shaft.

However, the wording 'bevel' might also enclose similar structures at the tip of the needle, which structures are useful for introducing the needle into a tissue. For example, the bevel might be a convex or concave surface, or the bevel might be a combination of several small surfaces, wherein these surfaces are connected to each other by steps or edges. It might also be possible that the cross section of the shaft is not completely cut by the bevel, such that an area remains which is blunt, i.e. is perpendicularly orientated relative to the longitudinal axis of the shaft. Such a 'blunt' end might include rounded edges or might also form a rounded leading edge. As another exemplary, a sharp edge might be formed by two or more slanted surfaces being symmetrically or asymmetrically arranged to form the tip of the needle.

According to one embodiment of the invention, the bevel forms an acute angle with the shaft, such that the needle includes a pointed tip. Preferably, the acute angle is approximately 20°.

According to one embodiment of the invention, the shaft of the needle has an outer diameter, and the end surface of the first fiber and the end surface of the second fiber are arranged at a distance to each other. Preferably, the distance between the fiber ends is greater than the diameter of the shaft. For example, the distance is more than 1.1 times greater than the diameter. Particularly, the distance is more than 1.25 times greater than the diameter. Preferably, the distance is more than 1.5 times greater than the diameter.

Depending on the intended use of the needle, the outer diameter of the needle might be 2.108 mm for a brain biopsy needle, between 1.27 mm and 2.108 mm for a common biopsy needle or a neuro puncture needle, between 0.711 mm and 2.108 mm for a fine aspiration needle, between 0.711 mm and 1.473 mm for an epidural needle, and might be 2.108 mm or smaller for a needle electrode.

According to a further embodiment of the invention, the needle further comprises a third fiber which is capable of transmitting light, wherein an end surface of the third fiber is located at the bottom of the bevel in the vicinity of the end surface of the second fiber. In this case, the second fiber and the third fiber might be located beside the long axis of the bevel surface.

For example, with a needle diameter of 1.3 mm it might be possible that the distance between the fiber at the top of the bevel and one of the fibers at the bottom of the bevel might be 2.46 mm, and the distance between the two fibers at the bottom of the bevel might be 0.37 mm.

It is noted that the distances are measured from the central axis of one of the fibers to the central axis of the other one of the fibers.

According to another embodiment of the invention, the shaft of the needle is formed by an inner tube and an outer tube, wherein a space is provided between the inner tube and the outer tube, in which space the fibers are accommodated.

According to yet another embodiment of the invention, the needle with fibers might be use in a system for optical tissue inspection, wherein the system further comprises a light source connected with one of the fibers of the needle, a light detector connected with another one of the fibers of the needle, wherein light coming from the light source and being emitted from the end surface of the one of the fibers can be detected by the light detector when entering the other one of the fibers, a processing unit for processing the data from the light detector, and a monitor for visualization of the processed data.

In such a system, the fiber distal ends in the needle slanted bevel provide at least one source-detector fiber pair with a distance A that is larger than the outer diameter of the needle D, wherein A>1.1D or even A>1.25D, and preferably A>1.5D. If b is the tip angle of the needle bevel the following equation might count $$\frac{A}{D} > \frac{\sin b + 0.1}{\sin b} \quad (1)$$

In the case that the needle is provided with a first fiber at the top of the bevel, and with second and third fibers at the bottom of the bevel, the first fiber might be serve as a light source emitting light into surrounding tissue, and the second and third fibers might be two detector fibers collecting reflected light.

The invention might also be related to a computer program for the processing unit of the system according to the invention. The computer program is preferably loaded into a working memory of a data processor. However, the computer program may also be presented over a network like the worldwide web and can be downloaded into the working memory of a data processor from such a network. The computer program might control the emitting of light, might process the signals coming from the light detector at the proximal end of the detector fiber(s). These data might then be visualized at a monitor.

It has to be noted that embodiments of the invention are described with reference to different subject matters. In particular, some embodiments are described with reference to application steps whereas other embodiments are described with reference to devices or systems. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted in different figures, same or similar elements are provided with the same reference signs.

DETAILED DESCRIPTION OF EXEMPLARY EMBODIMENTS

Figure 1:
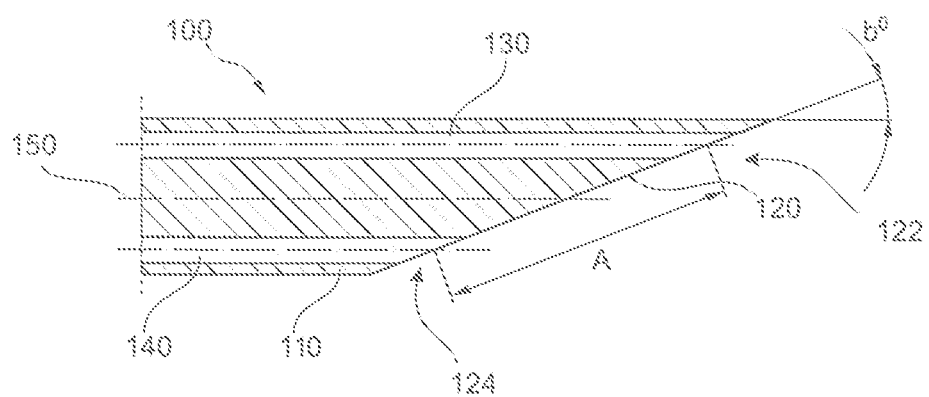
FIG. 1 shows a cross section of the tip portion of a needle according to a first embodiment of the invention.

FIG. 1 is a cross sectional view of the tip portion of a needle according to a first embodiment of the invention. The needle 100 includes a shaft 110 having a longitudinal axis or centre axis 150. Parallel to the centre axis, there are formed two bores or channels, in which fibers 130, 140 are located, respectively. These fibers, namely the first fiber 130 and the second fiber 140, include end surfaces 132, 142, respectively.

Further, the shaft 110 is cut at its distal end, such that a bevel 120 is formed. The bevel 120 is a slanted surface which can be divided in an area named as top 122 of the bevel, and an area named as bottom 124 of the bevel. Further, the bevel 120 enclose an angle b with the center axis of the shaft 110. The angle b is preferably an acute angle of approximately 20°.

The end surface 132 of the first fiber 130 is located at the top of the bevel and the end surface 142 of the second fiber 140 is located at the bottom of the bevel. After positioning the ends of the fibers in the channels or bores in the shaft, the bevel together with the ends of the fibers might be polished. By way of this, a smooth or even surface might be achieved including two end surfaces of fibers, wherein such polished end surfaces provide for good optical characteristics.

As further depict in FIG. 1, a distance A is defined, which is measured from a middle of the end surface 132 of the first fiber 130 to the middle of the end surface 142 of the second fiber 140.

Figure 2:
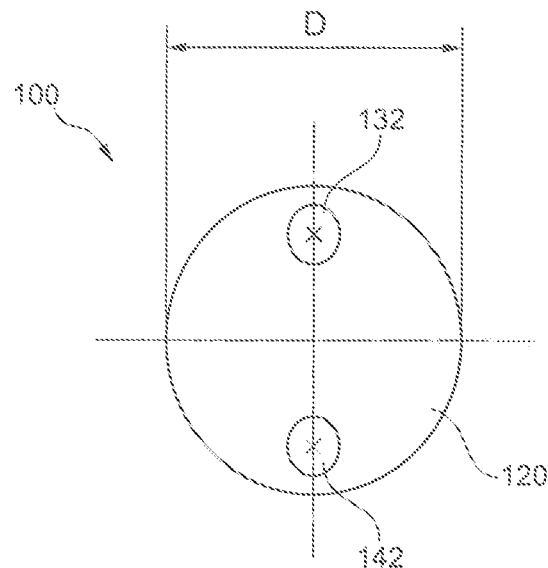
FIG. 2 shows a front view of the needle according to the first embodiment of the invention.

FIG. 2 is a front view of the needle according to the first embodiment of the invention. FIG. 2 shows the bevel 120 together with the end surface 132 of the first fiber and the end surface 142 of the second fiber. Furthermore, the usually circular cross section of the shaft of the needle 100 defines a diameter D. The distance A (see FIG. 1) is larger than the outer diameter D of the needle, wherein A>1.1D or even A>1.25D, and preferably A>1.5D.

With b as the tip angle of the bevel, the following equation might count $$\frac{A}{D} > \frac{\sin b + 0.1}{\sin b} \quad (1)$$

In the case of the first embodiment, in which the needle is provided with a first fiber at the top of the bevel, and with a second fiber at the bottom of the bevel, the first fiber might serve as a light source emitting light into surrounding tissue, and the second fiber might serve as a detector fiber collecting reflected light.

Figure 3:
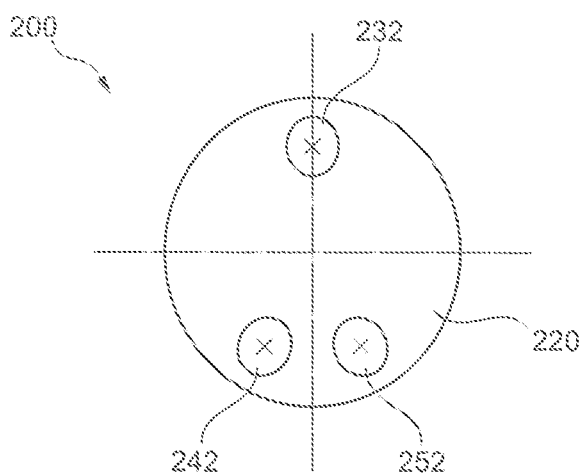
FIG. 3 shows a front view of a needle according to a second embodiment of the invention.

FIG. 3 is a front view of a needle according to a second embodiment of the invention. Generally, the second embodiment is similar to the first embodiment. The second embodiment also includes a shaft, a bevel forming an acute angle with the shaft, a first fiber at the top of the bevel, and a second fiber at the bottom of the bevel.

Additionally, the needle according to the second embodiment comprises a third fiber with an end surface 252. The third fiber is arranged in a channel or through bore which is formed parallel to the centre axis of the shaft and, thus, parallel to the channels of the first and second fibers. Further, the end surface 252 of the third fiber is located in the vicinity of the end surface of the second fiber, at the bottom 224 of the bevel 220.

In the case of the second embodiment, in which the needle is provided with a first fiber at the top of the bevel, and with second and third fibers at the bottom of the bevel, the first fiber might serve as a light source emitting light into surrounding tissue, and the second and third fibers might serve as detector fibers collecting reflected light.

Figure 4:
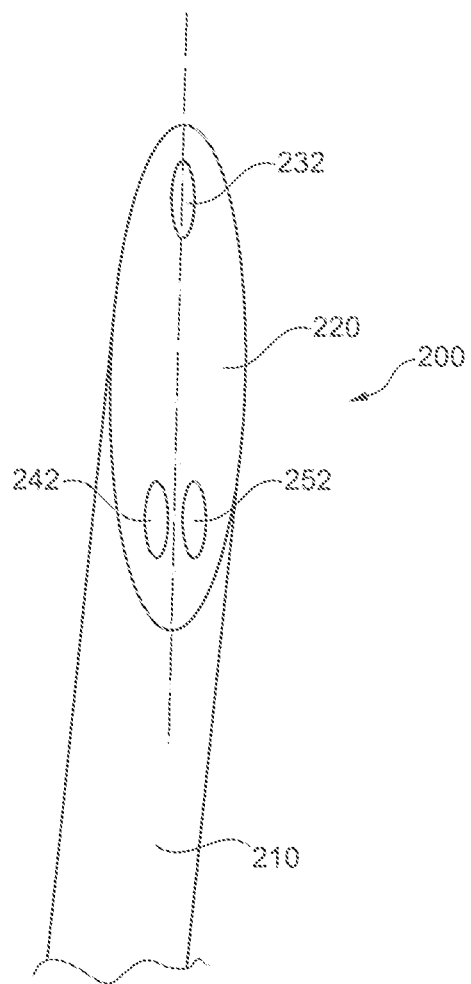
FIG. 4 is an isometric illustration of a tip portion of a needle according to the second embodiment of the invention.

FIG. 4 shows the tip portion of the needle according to the second embodiment as an isometric view. This view illustrates that the actual shape of the surface of the bevel as well as of the end surfaces of the fibers is substantially oval.

Figure 5:
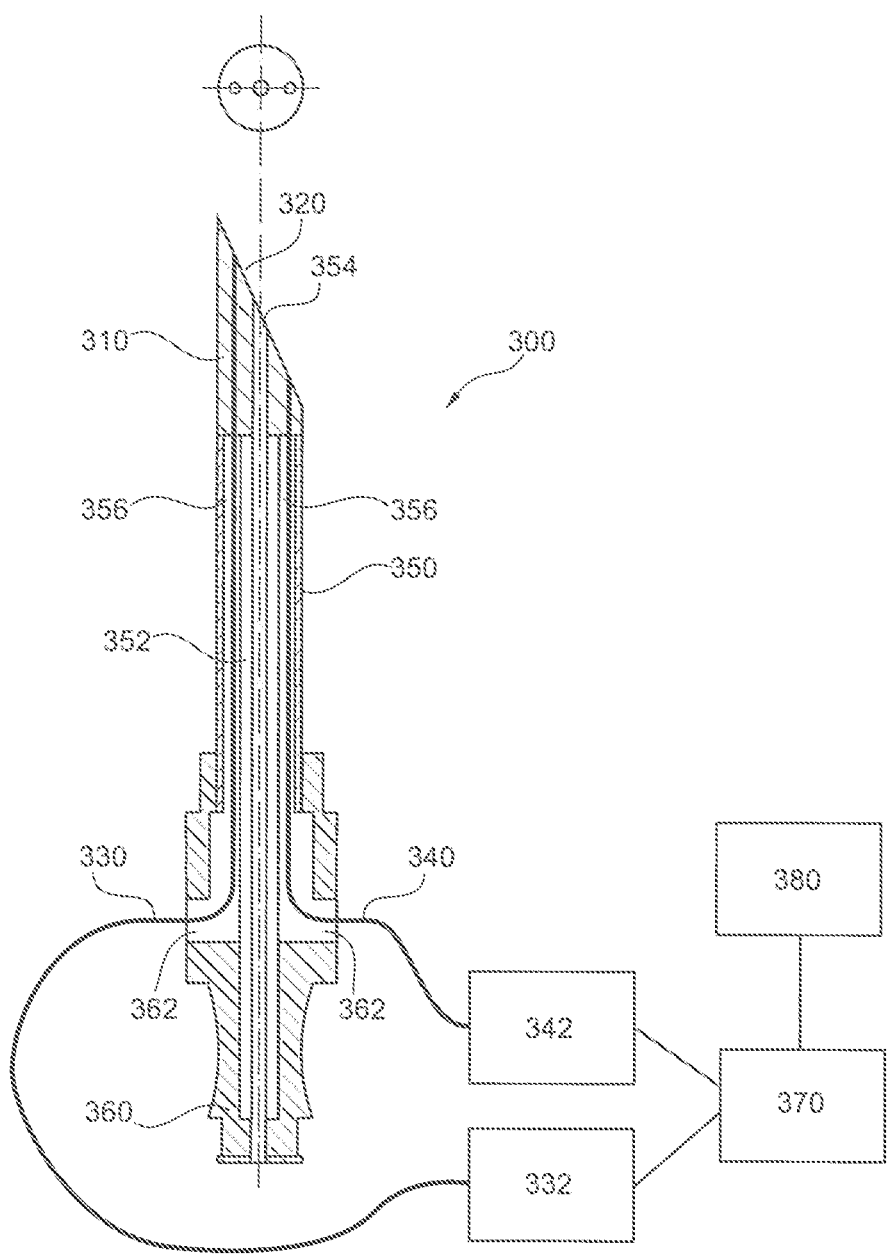
FIG. 5 is a schematic illustration of a system according to the invention, the system including a needle according to a third embodiment of the invention.

FIG. 5 illustrates a system according to the invention. The system includes a needle 300 according to a third embodiment of the invention. In this illustration, the needle 300 is an assembly of a tip part 310, an inner tube 352, an outer tube 350, and a holder part 360. Furthermore, two fibers 330 and 340 are shown in the needle.

An important part of the needle is the needle tip, in which two or three bores are manufactured. In each bore a fiber is mounted, by gluing. The tip is fixed to both inner tube and outer tube by welding or gluing, wherein the inner and outer diameters of the inner and the outer tube are adapted to correspond respective structures at the proximal shaft section of the tip part. A space 356 between the tubes might be achieved, into which the through bores in the tip part are open out. Coming out of the bores of the tip part, the fibers 330, 340 are positioned in the hollow space 356 between both tubes.

The tip, fibers and both tubes, once assembled, are fixed to a needle holder. Inside the holder the inner tube is connected with a connector to which for instance a syringe or other tubing can be fixed. In this way volumes of fluid can be dispensed through the channel 354 of the inner tube and tip part, without interaction with the fibers. The needle holder 360 also contains separate exit 362 for the fibers. After assembling tip, fibers, tubes and holder, the bevel 320 of the needle (i.e. the needle tip) is polished to obtain a proper surface quality for the fibers.

To have appropriate properties of the different parts of the needle, the tip part might be made of a metal, an alloy or ceramic material, and the shaft tubes might be made of a metal material, wherein the metal material should be MRI compatible, for example titanium.

Further, the system comprises a light source 332, a light detector 342, a processing unit 370 and a monitor 380. The processing unit 370 is capable of controlling the light source 332 to emit light into the fiber 330 such that light will be emitted through the distal end surface of the fiber 330 at the top of the bevel 320 into surrounding tissue. Depending on what kind of tissue is in front of the bevel, more or less of the emitted light will be reflected in the direction of the bottom of the bevel, to be received be the other fiber 340. Through the fiber 340, the light will is led to the light detector 342, which detector is adapted to transform the light into electrical signals. These electrical signals will be send by, for example, wire to the processing unit. The processing unit will process the data corresponding to the electrical signals, so that the processed data might be visualized on a monitor 380. Based on said visualized data, it might be possible to diagnose whether or not a tissue is cancerous.

In the following, exemplary needles according to the invention will be described with respect to their outer diameter, their insertion length, and their preferred use.

A biopsy needle might have an outer diameter of 1.27 mm up to 2.108 mm, might be inserted into tissue with 100 mm to 150 mm of its length, and might be used in soft tissue core biopsies in the neck, the head, the breast, the prostate, and the liver.

A fine aspiration needle of soft tissue might have an outer diameter between 0.711 mm and 2.108 mm, might be inserted into soft tissue with 100 mm to 150 mm of its length, and might be used for aspiration of soft tissue.

A brain biopsy needle might have an outer diameter of 2.108 mm, might be inserted into tissue with 150 mm up to 250 mm of its length, and might be used for diagnostic brain biopsies.

A neuro puncture needle might have an outer diameter of 1.27 mm up to 2.108 mm, might be inserted into tissue with 150 mm to 200 mm of its length, wherein such needles allow a non-traumatic approach to lesions in the brain.

An epidural needle might have an outer diameter between 0.711 mm and 1.473 mm, might be inserted into tissue with a length of up to 150 mm, and might be used for treatments in the spinal cord area such as steroid injections in the epidural space.

Finally, a needle electrode might have an outer diameter of 2 108 mm and smaller, might be inserted into tissue up to 250 mm of its length, and might be used for radiofrequency ablation for instance of tumors.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A processing unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together

LIST OF REFERENCE SIGNS 100, 200, 300 needle
110, 210 shaft
120, 220, 320 bevel
122 top of the bevel
124, 224 bottom of the bevel
130, 330 first fiber
132, 232 end surface of first fiber
140, 340 second fiber
142, 242 end surface of second fiber
150 longitudinal axis of needle
252 end surface of third fiber
310 tip part
332 light source
342 light detector
350 outer tube
352 inner tube
354 channel
356 space between inner and outer tubes
360 holder part
362 opening
370 processing unit
380 monitor

The invention claimed is:

1. A needle, comprising: a shaft;
a tip at a distal end of the shaft, wherein the tip of the needle is formed by a bevel; a first fiber, the first fiber configured to transmit light, wherein an end surface of the first fiber is located at a top of the bevel;
a second fiber configured to receive light, wherein an end surface of the second fiber is located at a bottom of the bevel;
a third fiber, configured to receive light, wherein an end surface of the third fiber is located at the bottom of the bevel in the vicinity of the end surface of the second fiber;
wherein the structure of the needle meets the following equation $$\frac{A}{D} > \frac{\sin b + 0.1}{\sin b};$$

wherein A is a distance measured from a middle of the end surface of the first fiber to a middle of the end surface of the second fiber and a distance measured from the middle of the end surface of the first fiber to the middle of the end surface of the third fiber; wherein D is the outer diameter of the shaft; and wherein b is the tip angle of the bevel.

2. The needle of claim 1, wherein the distance (A) is greater than the diameter (D).

3. The needle of claim 2, wherein the distance (A) is more than 1.5 times greater than the diameter (D).

4. The needle of claim 2, wherein the outer diameter (D) of the shaft is between 0.711 mm and 2.108 mm.

5. The needle of claim 1, wherein the bevel forms an acute angle (b) with the shaft, such that the needle includes a pointed tip.

6. The needle of claim 5, wherein the acute angle (b) is 20°.

7. The needle of claim 1, further comprising:
an inner tube and an outer tube,
wherein a space is formed between the inner tube and the outer tube, and
wherein the fibers are accommodated in the space.

8. A system for optical tissue inspection, the system comprising:
a needle according to claim 1;
a light source connected with the first fiber of the needle;
a light detector connected with one of the second fiber or the third fiber of the needle;
wherein light coming from the light source and being emitted from the end surface of the first fiber of the needle is detectable by the light detector when entering the one of the second fiber or the third fiber of the needle; and
a processing unit for processing the data from the light detector, and a monitor for visualization of the processed data.

9. A needle, comprising
a shaft having an outer diameter (D);
a tip at a distal end of the shaft, wherein the tip of the needle is formed by a bevel;
a first fiber configured to transmit light,
wherein an end surface of the first fiber is located at a top of the bevel;
a second fiber configured to transmit light,
wherein an end surface of the second fiber is located at a bottom of the bevel,
wherein an end surface of the first fiber and the end surface of the second fiber are arranged at a distance (A) to each other, and
wherein the distance (A) is greater than the diameter (D); and
a third fiber, configured to transmit light, wherein an end surface of the third fiber is located at the bottom of the bevel in the vicinity of the end surface of the second fiber.

10. The needle of claim 9,
wherein the end surface of the first fiber and the end surface of the third fiber are arranged at the distance (A) to each other.

11. The needle of claim 9, wherein the distance (A) is more than 1.5 times greater than the diameter (D).

12. The needle of claim 9, wherein the outer diameter (D) of the shaft (110, 210) is between 0.711 mm and 2.108 mm.

13. The needle of claim 9, wherein the bevel forms an acute angle (b) with the shaft, such that the needle includes a pointed tip.

14. The needle of claim 13, wherein the acute angle (b) is 20°.

15. The needle of claim 9, further comprising:
an inner tube and an outer tube,
wherein a space is formed between the inner tube and the outer tube, and
wherein the fibers are accommodated in the space.

16. A system for optical tissue inspection, the system comprising:
a needle according to claim 9;
a light source connected with the first fiber of the needle;
a light detector connected with the second and third fibers of the needle, wherein light coming from the light source and being emitted from the end surface of the first fiber can be detected by the light detector when entering the second and third fibers;

a processing unit for processing the data from the light detector, and a monitor for visualization of the processed data.

\* \* \* \* \*